United States Patent [19]

Suppelsa et al.

[11] Patent Number: 5,771,004
[45] Date of Patent: Jun. 23, 1998

[54] GAS DETECTION SYSTEM FOR A PORTABLE COMMUNICATION

[75] Inventors: Anthony J. Suppelsa, Coral Springs; Michael F. Shaw, Sunrise; Anthony B. Suppelsa, Coral Springs, all of Fla.

[73] Assignee: Motorola, Inc., Schaumburg, Ill.

[21] Appl. No.: 870,222

[22] Filed: Jun. 6, 1997

[51] Int. Cl.[6] .................................................. G08B 17/10
[52] U.S. Cl. ........................... 340/632; 340/632; 340/521
[58] Field of Search ................................... 340/632, 521; 381/24; D23/384; 73/24.01, 31.02, 31.03, 31.04, 729.1

[56] References Cited

U.S. PATENT DOCUMENTS

| | | | |
|---|---|---|---|
| 3,445,669 | 5/1969 | Jordan et al. | 250/218 |
| 4,263,588 | 4/1981 | Gautier | 340/632 |
| 4,297,689 | 10/1981 | Shaw et al. | 340/632 |
| 4,688,021 | 8/1987 | Buck et al. | 340/521 |
| 4,890,666 | 1/1990 | Clark | 165/16 |
| 5,311,570 | 5/1994 | Grimes et al. | 379/57 |
| 5,379,026 | 1/1995 | Whittle | 340/632 |
| 5,406,038 | 4/1995 | Reiff et al. | 181/167 |
| 5,406,265 | 4/1995 | Trozzo et al. | 340/632 |

*Primary Examiner*—Jeffery A. Hofsass
*Assistant Examiner*—Toan N. Pham
*Attorney, Agent, or Firm*—Glenn E. Gold; Dale W. Dorinski

[57] ABSTRACT

A hazardous gas detection system is integrated into a wireless communication device such as a two-way radio. The radio has housing (102) with an opening (104) for receiving external air. A bellows-like device (114) has a first side (116) which is attached to an audio speaker diaphragm (112) by a rigid interconnect element (126). A fixed second side (118) of the bellows has first and second ports, 120 and 122. Vibrations from the speaker diaphragm are transferred to the bellows, causing the bellows to expand and contract. During bellows expansion, air is sucked into a first port (120) of the bellows. As the bellows contracts, the air is forced out through a second port (122) of the bellows and directed toward a gas sensor (132) mounted on an internal surface (106) of the radio housing. A warning mechanism in communication with the gas sensor provides forewarning of dangerously high gas concentration levels.

9 Claims, 3 Drawing Sheets

GAS DETECTION SYSTEM FOR A PORTABLE COMMUNICATION

TECHNICAL FIELD

This invention relates in general to the monitoring of gas content in atmospheres, and more particularly to a portable communication device having an integral gas detection system.

BACKGROUND

There are many environments in which it is desirable to monitor the concentration of gases in the atmosphere and to provide an alarm when the concentration becomes excessive, or when there is an abnormal change in concentration, so that action may be taken to preclude a potentially harmful result. For example, excessive concentrations of flammable gases may result in a fire or explosion; similarly, excessive concentrations of toxic gases may result in a health hazard. The most common means of addressing such dangers is to install permanently fixtured gas monitoring devices (i.e., gas sensors) at specific locations in the vicinity of such potentially hazardous environments. However, due to a variety of factors, such as the time, labor and expense often associated with the installation of gas monitoring systems, environments commonly exist which, although susceptible to one or more of the above enumerated dangers, do not contain any such safety mechanism. As a result, countless individuals are exposed to potentially deadly gas-related risks with little or no means of receiving forewarning of said risks. The myriad types of environments in which such gas-related hazards may exist vary greatly. For example, such hazardous environments may range from work-related sites which produce hazardous gases for—or as a byproduct of—manufacturing processes, to personal residences having appliances which use natural gases or products which emit harmful gases, e.g., carbon monoxide emitted from an automobile housed in a garage.

Attempts have been made to provide non-fixtured detection systems capable of detecting dangerous gas levels. For example, U.S. Pat. No. 5,446,445 describes gas detecting sensors integrated into a wireless mobile detection system. The system comprises sensors mounted upon a selfpropelled movable robot. However, due to its relatively large size such a system may not be readily portable, e.g., to a work site. Furthermore, even an individual portable gas device, dedicated solely to gas detection, and conveniently transportable would likely prove ineffective and impractical in many situations, since individuals are often exposed to dangerous atmospheres unwittingly and, as a result, would often lack the impetus to carry such a device on their person.

For the foregoing reasons, it would be desirable to provide a gas monitoring system which is not only portable, but one which is likely to be carried on one's person despite the absence of a specific motive for doing so, i.e., fear of a gas-related harm.

DETAILED DESCRIPTION OF THE PREFERRED EMBODIMENT

Figure 1:
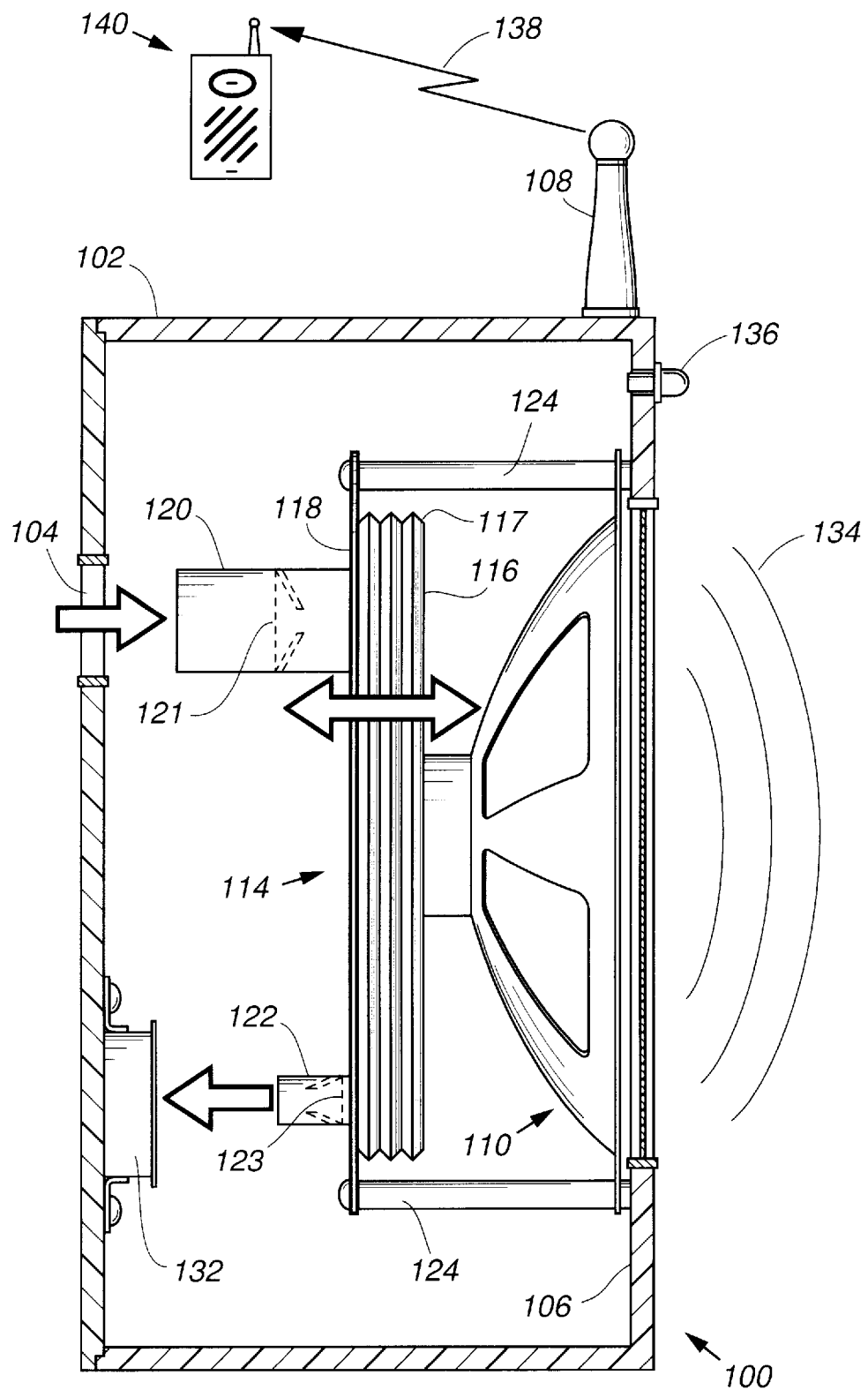
FIG. 1 is a cross-sectional view of a wireless two-way radio having an integral gas detection system, in accordance with the present invention.

While the specification concludes with claims defining the features of the invention that are regarded as novel, it is believed that the invention will be better understood from a consideration of the following description in conjunction with the drawing figures, in which like reference numerals are carried forward.

Referring now to FIG. 1, a wireless communication device having an integral gas detection system is shown. The integration of a gas detection system into a portable communication device provides distinct advantages over existing gas detection systems. For example, because the detection system is contained within a device designed to be carried upon one's person, portability is not an issue. Furthermore, since users of wireless communication devices generally require constant access to the devices, i.e., for ready communication, they are prone to carrying such devices on their person continuously. As a result, a wireless communication device having an integral gas detection system provides users with a hazardous gas detection / warning system, even during situations where users may have no reason to suspect the need for such a concern.

Although we envision the potential integration of our gas detection system into any of a number of portable wireless communication products, our preferred embodiment comprises a gas detection system integrated into a two-way radio. The two-way radio 100 has a radio housing 102 with a passageway 104 formed therethrough. The passageway provides a means for introducing external air into the housing. Although the passageway 104 is depicted as a single opening, the invention is not so limited; for instance, a vent or grill having a plurality of openings would suffice. Once introduced into the housing 102, air is directed toward a gas sensor 132 via an air circulation means. As one skilled in the art will recognize, a variety of mechanisms could be employed for providing air circulation inside of the housing. In the preferred embodiment, however, we describe a bellows 114 which functions as the air circulation means.

The bellows 114 comprises first and second sides, 116 and 118 respectively, connected by accordion-like side walls 117 which allow for alternating contraction and expansion of the bellows. The second side 118 is fixedly attached to an internal surface 106 of the housing 102, precluding movement of the second side. Attachment may comprise any of a number of well known fastening mechanism, e.g., screws, rivets, adhesives, etc. In the preferred embodiment, the second side may be fastened to the housing internal surface 106 using at least one rigid standoff 124. The second side 118 further includes first and second ports, 120 and 122, extending away from the bellows toward the rear of the radio 100. The first port 120 functions as an air inlet for drawing air into the bellows, while the second port 122 acts as an outlet for directing air flow toward the gas sensor 132. Preferably, the first port 120 is axially aligned with the passageway 104 in the housing, such that air entering the housing is directed toward the first port. Similarly, the second port 122 should be axially aligned with the gas sensor 132 such that air expelled from the bellows 114 flows directly toward the gas sensor.

Figure 2:
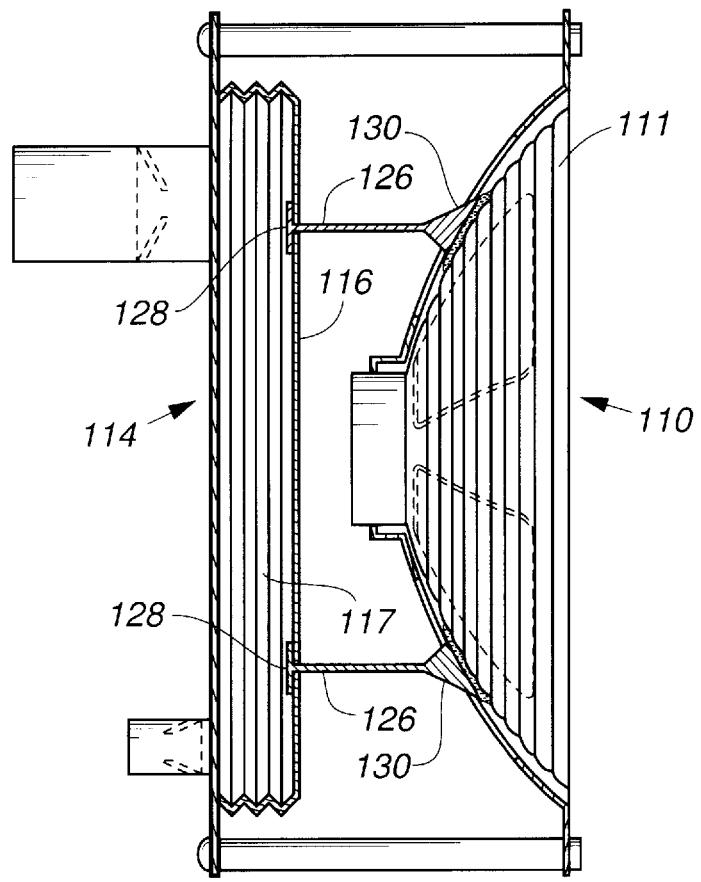
FIG. 2 is a cross-sectional view illustrating the use of an audio speaker cone as a source for vibration of the bellows, in accordance with the present invention.
Figure 3:
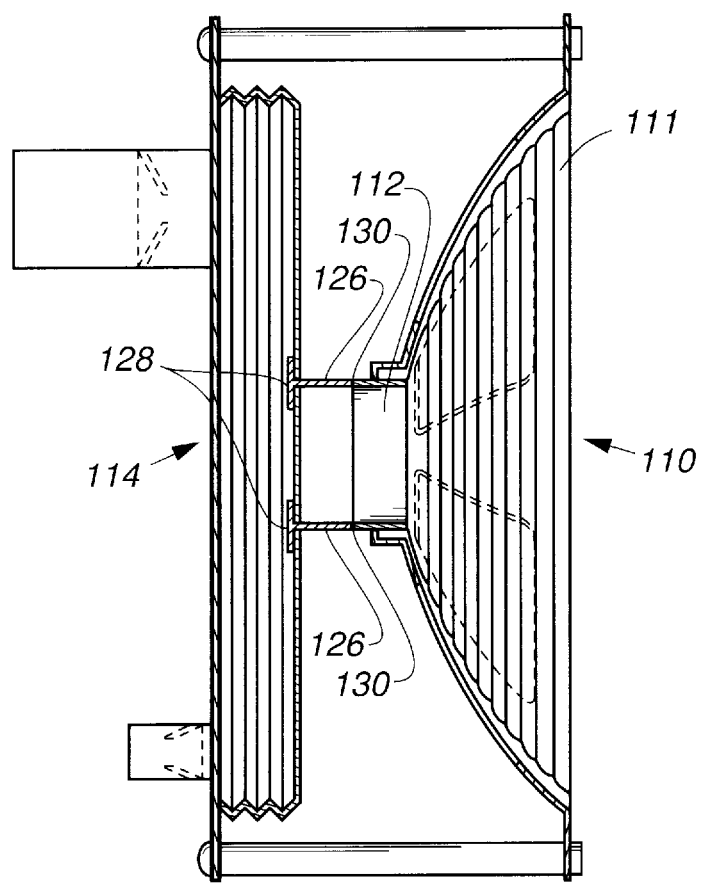
FIG. 3 is a cross-sectional view illustrating the use of a voice coil as a source for vibration of the bellows, in accordance with the present invention.

Referring now to both FIG. 2 and FIG. 3, an illustration of the interconnection of the bellows to the audio speaker is shown. The first side 116 of the bellows 114 is attached to a vibrating component of the audio speaker 110. As shown in FIG. 2, the vibrating component may comprise a speaker cone 111 portion of the audio speaker 110. Alternatively, as shown in FIG. 3, a further embodiment employs a voice coil 112 component of the audio speaker for vibration. Attachment may be achieved using a pair of rigid interconnect elements 126, each having a first end 128 connected to the first side 116 of the bellows 114 and a second end 130 connected to the vibrating portion, 111 or 112, of the audio speaker 110. Vibration of the aforementioned speaker components, i.e., the voice coil and speaker cone, occur naturally when audio signals are received by the radio. The vibrations are imparted from the vibrating portion, 111 or 112, of the audio speaker 110, through the rigid interconnect element 126, to the bellows first side 116, effecting alternating contraction and expansion of the side walls 117.

Referring back to FIG. 1, as the side walls 117 expand, a first valve 121 in the first port 120 opens such that air is drawn into the bellows; simultaneously, a second valve 123 in the second port 122 is forced shut. Subsequent contraction of the side walls 117 causes the first valve 121 to close and the second valve 123 to open, forcing the air out of the bellows, through the second port 122, toward the gas sensor 132. The gas sensor samples the air to determine concentration levels of a particular gas(es). A single gas sensor capable of detecting a variety of gases may be employed. Alternatively, a plurality of gas sensors, capable of detecting multiple different gas types may be used.

A warning mechanism may be employed to signal a high gas concentration level, i.e., provide forewarning of a potentially hazardous situation. The warning mechanism is in constant communication with the gas sensor 132, e.g., via internal radio circuitry (not shown). The warning mechanism may comprise a variety of embodiments. For example, in one embodiment, the warning mechanism comprises an audible signal 134, such as a high pitch beep, transmitted through the audio speaker 110. Here, the term 'audible signal' refers to a sound audible to the human ear. In a further embodiment, the warning mechanism comprises a visual signal 136, e.g., a light emitting diode (LED) mounted upon an external surface of the radio housing. Such a visual signal may be beneficial in situations where those nearby are unable to recognize an audible signal. In yet a further embodiment, the warning mechanism comprises a radio frequency (RF) signal 138 transmitted via an antenna 108 on the radio to a remote communication device 140, such as a base station or two-way radio. Receipt of the RF signal preferably results in a warning signal at the remote communication device. In addition, any combination of the aforementioned warning mechanisms could be simultaneously employed.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as defined by the appended claims. For example, we contemplate an embodiment of the invention having internal circuitry for periodically vibrating the audio speaker (and thus bellows) to ensure sufficient sampling of the external air, in instances where the frequency, i.e., recurrence, of received audio signals is insufficient to provide adequate sampling. Furthermore, those skilled in the art will appreciate that an electromechanical device such as a miniature fan contained within the device housing could be used in lieu of a bellows device for drawing air into the housing and subsequently directing it toward the gas sensor.

What is claimed is:

1. A gas detection system for a wireless communication device, the device having an integral audio speaker, the gas detection system comprising:
    a device housing having a passageway formed therethrough;
    a gas sensor fixedly attached to an internal surface of said device housing;
    a bellows having first and second sides, the second side fixedly attached to the internal surface of the device housing, said bellows further having first and second ports extending from the bellows second side, the first port for drawing air into said bellows and the second port for directing air out of said bellows toward said gas sensor; and
    at least one rigid interconnect element having first and second ends, the first end attached to the first side of said bellows and the second end attached to a vibrating portion of the audio speaker,
        wherein vibrations imparted from the vibrating portion of the audio speaker, through said at least one rigid interconnect element, to the bellows first side, effect alternating contraction and expansion of the bellows, resulting in air movement directed toward said gas sensor.

2. The gas detection system of claim 1, wherein said wireless communication device comprises a two-way radio.

3. The gas detection system of claim 1, wherein said vibrating portion of the audio speaker comprises a speaker cone.

4. The gas detection system of claim 1, wherein said vibrating portion of the audio speaker comprises a voice coil.

5. The gas detection system of claim 1, further comprising a warning mechanism in communication with said gas sensor, said warning mechanism for signaling the existence of a hazardous gas concentration.

6. The gas detection system of claim 5, wherein said warning mechanism comprises an audible signal transmitted through said audio speaker.

7. The gas detection system of claim 5, wherein said warning mechanism comprises a visual signal.

8. The gas detection system of claim 1, wherein said warning mechanism comprises an RF signal transmitted from said wireless communication device to a remote communication device, said RF signal generating a warning signal at said remote communication device.

9. A two-way radio having an audio speaker, comprising:
    a radio housing having a passageway formed therethrough;
    a gas sensor fixedly attached to an internal surface of said radio housing;
    a bellows for providing air circulation internal to said radio housing, said bellows having first and second sides,
        the first side attached to a vibrating portion of the audio speaker by at least one rigid interconnect element having first and second ends, the first end of said rigid interconnect element fixedly attached to the first side of said bellows and the second end fixedly attached to the vibrating portion of the audio speaker, the second side fixedly attached to the internal surface of the radio housing by at least one rigid standoff;

first and second ports extending from the second side of said bellows, said first port axially aligned with the passageway in said housing, and said second port axially aligned with said gas sensor; and a warning mechanism in communication with said gas sensor, wherein vibrations imparted from the vibrating portion of the audio speaker, through said rigid interconnect element, to the bellows first side, effect alternating contraction and expansion of the bellows, and wherein alternating expansion and contraction of the bellows results in air movement directed toward said gas sensor.

* * * * *